United States Patent [19]

Hauser

[11] Patent Number: 5,462,859
[45] Date of Patent: Oct. 31, 1995

[54] METHOD OF DIAGNOSING IRREGULARITIES IN BILE SALT ABSORPTION VIA BRUSH BORDER MEMBRANE PROTEINS

[76] Inventor: Helmut Hauser, Laboratorium fur Biochemie, ETH-Zentrum, Universitatstrasse 16, CH-8092 Zurich, Switzerland

[21] Appl. No.: 61,372

[22] Filed: May 14, 1993

[51] Int. Cl.$^6$ .................................................... C12Q 1/02
[52] U.S. Cl. ........................ 435/29; 436/63; 436/501; 436/504; 436/811
[58] Field of Search .................. 436/57, 504, 501, 436/545, 56, 804, 811, 63; 435/29

[56] References Cited

U.S. PATENT DOCUMENTS

| | | | |
|---|---|---|---|
| 4,760,135 | 7/1988 | Diedrich et al. | 536/17.9 |
| 4,769,334 | 9/1988 | Fleming | 436/57 |
| 4,806,532 | 2/1989 | Dousa | 514/120 |
| 4,863,852 | 9/1989 | Wilkins et al. | 435/7 |
| 4,908,321 | 3/1990 | Varma | 436/57 |
| 5,120,641 | 6/1992 | Hashimoto et al. | 436/57 |

OTHER PUBLICATIONS

Brunner, J. et al. "Single Bilayer Lipid–Protein Vesicles Formed from Phosphatidylcholine and Small Intestinal Sucrase–Isomaltase", *J. Biol. Chem.*, vol. 235, No. 20, (1978) pp. 7538–7546.
Kessler, M. et al. "A Modified Procedure for the Rapid Preparation of Efficiently Transporting Vesicles from Small Intestinal Brush Border Membranes: Their Use in Investigating Some Properties of $_D$–Glucose and Choline Transport Systems", *Biochimica et Biophysica Acta*, vol. 506, (1978) pp. 136–154.
Hauser, H. et al. "Rabbit Small Intestinal Brush Border Membrane Preparation and Lipid Composition", *Biochimica et Biophysica Acta*, vol. 602, (1980) pp. 567–577.
Hauser, H. et al. "Orientation and Motion of Spin–Labels in Rabbit Small Intestinal Brush Border Vesicle Membranes", *Biochemistry*, vol. 21, (1982) pp. 5621–5628.
Child, P. et al. "Uptake of 7–dehydro Derivatives of Cholesterol, Campesterol, and β–sitosterol by Rat Erythrocytes, Jejunal Villus Cells, and Brush Border Membranes", *J. Lipid Res.*, vol. 24, (1983) pp. 552–565.
Ikeda, I. et al. "Some Aspects of Mechanism of Inhibition of Cholesterol Adsorption by β–Sitosterol ", *Biochemica et Biophysica Acta*, vol. 732, (1983) pp. 651–658.
Proulz, P. et al. "The Effect of Phosphoglycerides on the Incorporation of Cholesterol into Isolated Brush–Border Membranes from Rabbit Small Intestine", *Biochimica et Biophysica Acta*, vol. 775, (1984) pp. 341–346.
Lasic, D. D. et al. "The Potential of Electron Spin Resonance Spin–Labeling in Determining Micelle Shapes", *J. Physical Chem.*, vol. 89, No. 12, (1985) pp. 2648–2651.
Proulx, P. et al. "Studies on the Uptake of Fatty Acids by Brush Border Membranes of the Rabbit Intestine", *Can. J. Biochem. Cell Biol.*, vol.63, (1985) pp. 249–255.
Vallet—Strouve, C. et al. "Effect of Micellar Lipids on Rabbit Intestinal Brush–Border Membrane Phospholipid Bilayer Integrity Studied by$^{31}$P NMR", *J. Membrane Biol.*, vol. 84, (1985) pp. 73–79.
Mütsch, B. et al. "Interaction of Intestinal Brush Border Membrane Vesicles with Small Unilamellar Phospholipid Vesicles. Exchange of Lipids between Membranes is Mediated by Collisional Contact", *Biochemistry*, vol. 25, (1986) pp. 2134–2140.
Proulx, P. et al. "Factors Influencing the Uptake of Cholesterol by Isolated Brush Border Membranes from Rabbit Small Intestine", *Exp. Biol.*, vol. 45, (1986) pp. 335–343.
Tellier, C. et al. "Interactions between Biliary Lipid Micelles and Intestinal Brush Border Membranes Investigated by$^1$H and$^{31}$P Nuclear Magnetic Resonance", *Eur. Biophys. J.*, vol. 15 (1987) pp. 177–184.
Ikeda, I. et al. "Inhibition of Cholesterol Absorption in Rats by Plant Sterols", *J. Lipid Res.*, vol. 29, (1988) pp. 1573–1582.
Ikeda, I. et al. "Discrimination between Cholesterol and Sitosterol for Absorption in Rats", *J. Lipid Res.*, vol. 29, (1988) pp. 1583– 1591.
Chijiiwa, K. et al. "Bile Salt Micelle Can Sustain More Cholesterol in the Intermicellar Acqueous Phase than the Maximal Acqueous Solubility", *Arch. Biochem. Biophys.*, vol. 270, No. 2, (1989) pp. 472–477.
Thurnhofer, H. et al. "Uptake of Cholesterol by Small Intestinal Brush Border Membrane Is Protein–Mediated", *Biochemistry*, vol. 29, (1990) pp. 2142–2148.
Thurnhofer, H. et al. "The Uptake of Phosphatidylcholine by Small Intestinal Brush Border Membrane is Protein–Mediated", *Biochimica et Biophysica Acta*, vol. 1024, (1990) pp. 249–262.
Lipka, G. et al. "Lipid Asymmetry in Rabbit Small Intestinal Brush Border Membrane as Probed by an Intrinsic Phospholipid Exchange Protein", *Biochemistry*, vol. 30, (1991) pp. 11828–11836.
Thurnhofer, H. et al. "Cholesterol–Transfer Protein Located in the Intestinal Brush–Border Membrane. Partial Purification and Characterization", *Biochimica et Biophysica Acta*, vol. 1064, (1991) pp. 275–286.
Thurnhofer, H. et al. "Membrane Proteins Exposed on the External Side of the Intestinal Brush–Border Membrane Have Fusogenic Properties", *Eur. J. Biochem.*, vol. 201, (1991) pp. 273–282.

*Primary Examiner*—Donald E. Czaja
*Assistant Examiner*—Lien Tran
*Attorney, Agent, or Firm*—Lowe, Price, Leblanc & Becker

[57] ABSTRACT

An isolated associated complex of bile acid salts and brush border membrane protein and a method of diagnosing irregularities in bile salt absorption via brush border membrane proteins is presented. In addition a method for detecting specific binding of bile salts to intestinal brush border membrane protein is disclosed.

3 Claims, 7 Drawing Sheets

10G

10G

10G

10G

10G

METHOD OF DIAGNOSING IRREGULARITIES IN BILE SALT ABSORPTION VIA BRUSH BORDER MEMBRANE PROTEINS

TECHNICAL FIELD

This invention relates to the interaction of bile salts with the brush border membrane of the intestinal tract.

More particularly, the present invention relates to the discovery that over half of the bile salt present in intestinal brush border membrane (BBM) is associated or complexed with BBM protein and not incorporated into the lipid bilayer of the BBM. Thus, the invention relates to an isolated associated complex of bile acids and brush border membrane protein and a method of diagnosing irregularities in bile salt absorption via brush border membrane proteins. The invention also provides a method for detecting specific binding of bile salts to intestinal brush border membrane protein.

BACKGROUND ART

Gastrointestinal fat digestion consists of three steps, (i) the dispersion of bulk fat into emulsion droplets, (ii) the enzymatic hydrolysis of fat at the emulsion-water interface and (iii) the desorption and dispersion of digested fats, which are still water-insoluble, into smaller particles of micelles suitable for fat absorption (Carey, M. C., Small, D. M., and Bliss, C. M. 1983. *Ann. Rev. Physiol.* 45, 651–677). The intestinal content during fat digestion and absorption consists therefore of two phases, an emulsified oil phase and a micellar phase (Hoffmann, A. F., and Small, D. M. 1967. *Ann. Rev. Med.* 18, 333–376).

Convincing evidence now exists that fat is chiefly absorbed by the BBM from the micellar phase containing bile salts, 2-monoacyl glycerols, fatty acids, cholesterol and phospholipids or their lyso derivatives (Borgstrom, 1962. *Gastroenterology*, 43,216–219; Senior, J. R. 1964. *J. Lipid Res.* 4, 109–130).

it is well-known that cholesterol and other lipids are most efficiently absorbed by the BBM in the presence of bile salts (Borgstrom, B. 1974. *Biomembranes (Smyth, D. H., Ed.)* 4B, 555–620, Plenum Press, New York; Thomson, A. B. R., and Dietschy, J. M. 1981. *Physiology of the Gastrointestinal Tract* (Johnson, L. R., Ed.) 1147–1220, Raven Press, New York; Thurnhofer, H. and Hauser, H. 1990. *Biochim. Biophys. Acta* 1024, 249–262). Bile diversion reduces the uptake of not only cholesterol, but also of other lipids such as 2-monoacylglycerols, fatty acids and phospholipids. There are several ways in which bile salt are considered to facilitate fat absorption as was pointed out before (for example, Thomson and Dietschy, J. M. 1981. *Physiology of the Gastrointestinal Tract* (Johnson, L. R., Ed.) 1147–1220, Raven Press, New York): (i) bile salt micelles solubilize the products of fat digestion and serve as a vehicle to bring these products close to the site of fat absorption. There is an equilibrium partitioning of the lipids between the micellar phase and the aqueous phase, and lipid monomers diffuse into the external lipid monolayer of the BBM. (ii) Bile salt micelles adsorb or bind to the luminal surface of the BBM and lipid molecules are either enzymatically or by diffusion incorporated into the BBM. (iii) Small bile salt micelles containing the products of fat digestion are incorporated as a whole into the BBM in a process akin to pinocytosis.

Previous studies by Wilson and Treanor (Wilson, F. A. and Treanor, L. L. 1977. *J. Membrane Biol.* 33, 213–230) concluded that the interaction of $^{14}C$-labeled taurodeoxycholate with BBM from rat small intestines is unspecific and independent of membrane proteins. These studies reflected the interaction of the bile salt with the lipid bilayer of the BBM. Their conclusions are based on the finding that boiling of the suspension of brush border membrane vesicles (BBMV) and proteolysis of BBM with trypsin had no effect on the extent of binding of the bile salt.

Klip et al. (Klip, A., Grinstein, S., and Semenza, G. 1979. *J. Membrane Biol.* 51, 47–73) showed by sodium dodecylsulfate polyacrylamide gel electrophoresis that not only lipids are extracted from BBMV in the presence of excess bile salt micelles but also proteins. Whether these proteins are liberated from the membrane by the activity of intrinsic proteinases of the BBM or whether integral membrane proteins are distributed into the micellar phase is not clear from the data of Klip et al.

U.S. Pat. No. 4,806,532 to Dousa discloses a method of inhibition of transport of phosphate across the epithelial cell membrane by contacting the epithelial cells with an effective amount of photophonoformic acid (PFA), for example. PFA is an inhibitor of sodium phosphate co-transport across the luminal brush border membrane of the renal proximal tubulars. Dousa does not recognize the existence of a mediating protein in the bile salt and brush border membrane reaction. Dousa is concerned with inhibiting salt transport.

U.S. Pat. No. 4,760,135 to Diedrich et al., discloses the inhibition of uptake by the BBM, and is directed to restricting the uptake of glucose and sugar. Diedrich et al. do not recognize the existence of the protein.

Ikeda et al. (Ikeda et al. 1988. *Journal of Lipid Research*, 29, 1573–1591) studies several parameters of cholesterol absorption including the effect of β-Sitosterol on micellar incorporation of cholesterol both in vitro and in vivo. Ikeda explains the discrepancy in the rate of absorption of cholesterol in vitro and in vivo by suggesting that cholesterol absorption proceeds through carrier mediated and/or energy dependant processes. Ikeda does not suggest what carrier mediated processes may be occurring.

Proulx et al. (Proulx et al. 1986. *Experimental Biology*, 45, 335–343) do not recognize the existence of a mediating protein but investigate the uptake of cholesterol by brush border membranes in the presence of a calcium cation. Proulx et al. are uncertain whether the effect of the calcium cation is to promote diffusion of cholesterol containing micelles with the brush border membrane, but suggests the calcium cation might promote micelle membrane interactions by masking negative charges at the reactant surfaces.

Tellier et al. (Tellier, C., Vallet-Strouve, C., Akoka, S., and Poignant, S. 1987. *Eur. Biophys. J.* 15, 177–184) investigates the relationship between bile salts and brush border membranes. Tellier et al. have discovered that taurocholate and other biliary salts produced considerable alteration in membranes except for brush border membranes. Tellier et al. have not investigated the reasons for this difference, but they do suggest that taurocholate interacts with brush border membrane bilayer. This publication teaches away from the existence of a protein mediating the reaction between bile salts and brush border membranes.

DISCLOSURE OF THE INVENTION

It is an object of the invention to provide an isolated associated complex comprising bile salts and Brush border membrane protein.

Another object of the present invention provides a method for detecting specific binding of bile salts to intestinal brush border membrane protein.

Still another object of the invention includes providing a method of diagnosing irregularities in bile salt absorption via brush border membrane proteins.

Still further objects of the invention will become apparent to those of skill in the art from the disclosure herein.

STATEMENT OF INVENTION

The invention provides an isolated composition comprising an associated complex of bile acids or salts thereof and a least one brush border membrane protein. The bile salt-BBM protein associated complex of the invention is useful for experimentation in and study of intestinal absorption. The composition may also be used in a method for detecting specific binding of bile salts to intestinal brush border membrane and in a method for diagnosing irregularities in bile salt absorption via proteins of the intestinal brush border membrane. The isolated composition may be incorporated into synthetic brush border membranes for pharmaceutical use.

Also disclosed is a method for detecting specific binding of bile salts to intestinal brush border membrane protein, including a) suspending an intestinal brush border membrane (BBM) sample in a suitable buffer; b) incubating said BBM with suitable concentrations of radiolabeled bile salt at room temperature for suitable period of time; c) centrifuging said BBM incubated with radiolabelled bile salt at about 80000 g for about 10 min.; d) measuring the amount of radiolabelled bile salt present in the BBM to determine the amount of composition of bile salt associated with said BBM protein.

The invention includes a method for diagnosing irregularities in bile salt absorption via proteins of the intestinal brush border membrane including a) suspending an intestinal brush border membrane (BBM) sample in a suitable buffer, b) incubating said BBM with suitable concentrations of radiolabeled bile salt at room temperature for suitable period of time, c) centrifuging said BBM incubated with radiolabelled bile salt at about 80000 g for about 10 min., d) measuring the amount of radiolabelled bile salt present in the BBM to determine the amount of composition of bile salt associated with the BBM, and e) comparing the amount measured in step (d) with a standard bile salt-BBM association value wherein a deficiency in the values represents an irregularities in bile salt absorption via proteins on intestinal brush border membrane. This method is useful in diagnosing intestinal absorption disorders.

DESCRIPTION OF THE INVENTION

Figure 1:
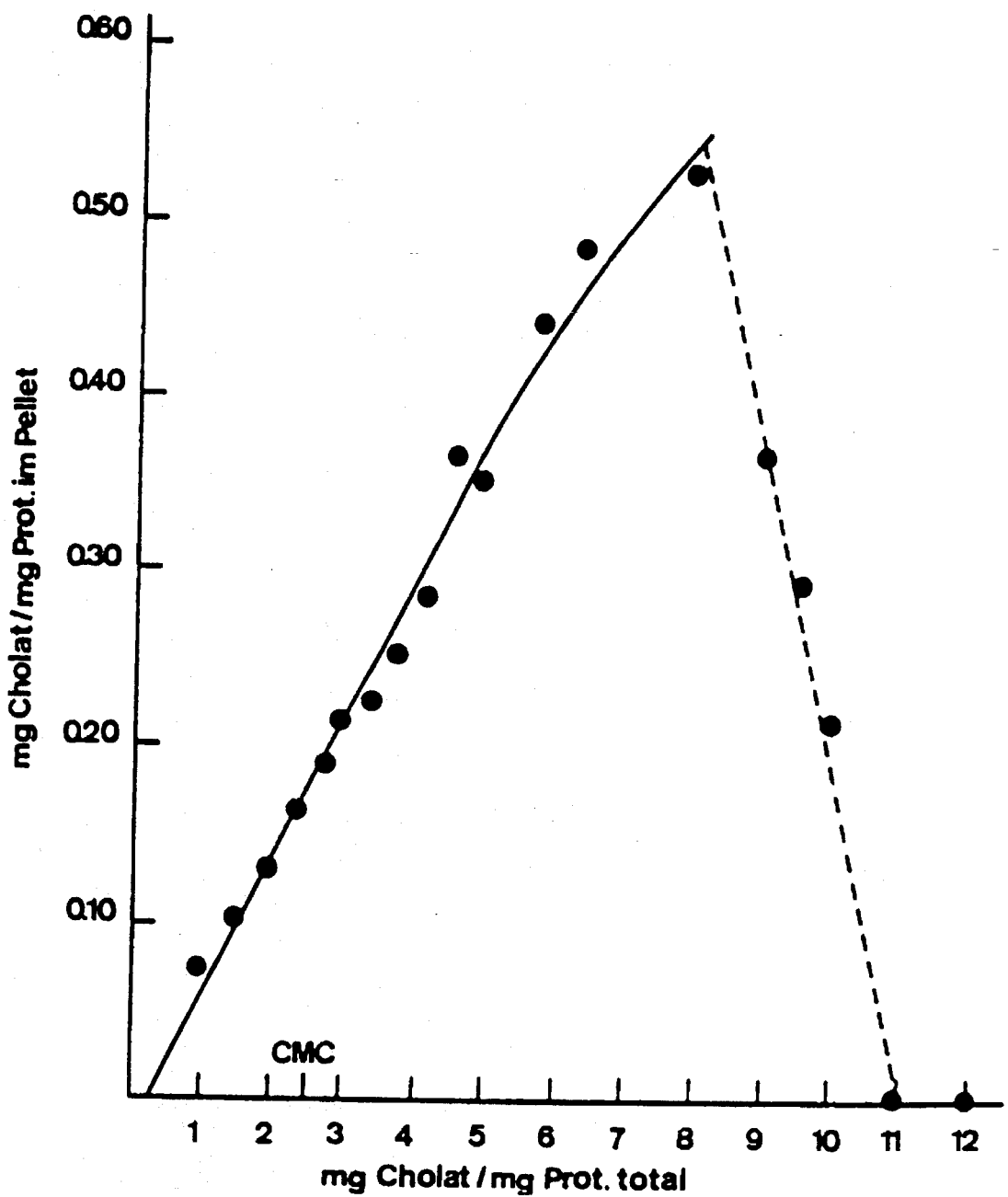
FIG. 1 shows an isotherm describing the interaction of sodium cholate with BBMV.

Thus prior to the present invention it was unclear whether intestinal absorption on the brush border membrane involved a bile salt-brush border membrane protein. The present inventors have advantageously isolated an associated complex comprising bile salts and brush border membrane protein and confirm its involvement in gastrointestinal fat digestion.

The present invention concerns the interaction of bile salts with brush border membrane. An in vitro system using brush border membrane vesicles prepared routinely from rabbit small intestines was used to study this interaction.

Brush border membrane vesicles (BBMV) are relatively resistant to bile salt. Solubilization of brush border membrane occurs at bile salt concentrations which are a multiple of their critical micellar concentration. This is quite different from the solubilization of phospholipid bilayers and other biological membranes which are less stable and undergo solubilization at free bile salt concentrations close to the critical micellar concentration.

The mechanism of solubilization of brush border membrane vesicles has been proposed to involve the incorporation of bile salt into the lipid bilayer of the brush border membrane and the simultaneous flow of brush border membrane components to the micellar phase. In excess bile salt micelles, these two processes lead to the destabilization of the brush border membrane with the formation of mixed bile salt micelles containing both lipids and proteins of the brush border membrane.

The invention shows that the interaction of bile salts with brush border membrane involves not only the non-specific distribution of bile salt into the lipid bilayer of this membrane, but more than half of the total bile salt associated with brush border membrane appears to be bound to protein. These are integral protein(s) and/or glycoprotein(s) exposed on the external or luminal surface of the brush border membrane.

Furthermore the present invention provides a method for detecting specific binding of bile salts to intestinal brush border membrane protein.

Finally the present invention and its discovery that a bile salt-brush border membrane protein complex is involved in gastrointestinal fat digestion, provides for a method of diagnosing irregularities in bile salt absorption via brush border membrane proteins.

An example of the experimental procedure and materials used in carrying out the best mode of the invention is set forth below.

Materials

Cholic acid and deoxycholic acid were purchased from Merck (Darmstadt, Deutschland). The $Na^+$ salt was obtained by adding the equivalent quantity of NaOH to the acid. The sodium salts of the two conjugated acids, taurocholic and glycocholic acids were obtained from Sigma (St. Louis, Mo.) and Calbiochem (Laufelfingen, Switzerland), respectively.

Cholic acid was recrystallized from acetone/water (4:1, v/v) and sodium taurocholate from ethanol/diethyl ether (17:40, v/v). Sodium deoxycholate and glycocholate were purified by preparative thin-layer chromatography (Lipka, G., OpdenKamp, J. A. F., and Hauser, H. 1991. *Biochemistry* 30, 11828–11836). The purity of the bile salts was checked routinely by thin-layer chromatography using ethylacetate/ methanol/acetic acid (7:2:1, v/v) or butanol/H$_2$O/ethanol (80:20:8, v/v) as the solvent.

Egg PC (phosphatidylcholine) was purchased from Lipid Products (Surrey, UK), 1,2-dipalmitoyl-sn-phosphatidyl[N-methyl-$^3$H]choline ($^3$H-DPPC, specific activity 76 Ci/mmol) was purchased from Amersham (Amersham, UK), [carboxyl-$^{14}$C]-cholic acid from NEN (Du Pont de Nemours International S.A., Regensdorf, Switzerland) and proteinases K from Tritirachium album from Boehringer (Mannheim, Deutschland). All other chemicals used were of analytical grade. All lipids used in this work were pure by thin-layer chromatography standards.

Methods

BBMV were prepared from rabbit small intestines according to Hauser, H., Howell, K., Dawson, R. M. C., and Bowyer, D. E. 1980. *Biochim. Biophys. Acta* 602, 567–577. The intestines were stored at –80° C. prior to the preparation of BBMV as described by Thurnhofer, H., Schnabel, J., Betz, M., Lipka, G., Pidgeon, C., and Hauser, H. 1991. *Biochim. Biophys. Acta* 1064, 275–286. BBMV were suspended in 0.01M Hepes buffer adjusted with Tris to Ph 7.5 and containing 0.3M mannitol, 5 Mm EDTA and 0.02% NAN$_3$, the suspension was frozen in liquid N$_2$ and stored at –35° C. prior to use.

BBMV suspended in Hepes/Tris (tris=tris-(hydroxymethyl) aminoethane) buffer at the desirable concentration were incubated with increasing concentrations of radiolabeled sodium cholate at room temperature for 15 min. After incubation BBMV were separated from bile salt by centrifugation at 80000 g for 10 min. in a Beckman airfuge. The radioactivity in both the supernatant and the pellet of BBMV was determined. To this end the supernatant was carefully decanted, the BBM pellet was dissolved in 2% Triton X-100 in the same Hepes/Tris buffer and aliquots of both the supernatant and solubilized BBM were counted in a Beckman LS 7500 liquid scintillation counter. The interaction of sodium cholate with BBMV was determined with freshly thawed BBMV, with BBMV which were stored for 2 hours at room temperature and BBMV digested with proteinase K (Thurnhofer, H. and Hauser, H. 1990. *Biochim. Biophys. Acta* 1024, 249–262) prior to the addition of bile salt.

BBMV suspended in Hepes/Tris buffer at the appropriate concentration were incubated with a sonicated egg PC dispersion in the same buffer at room temperature for ~2 hours. The small unilamellar egg PC vesicles contained $^3$H-DPPC or 5-doxyl-PC incorporated in their lipid bilayer. The experimental conditions were such that the final mole ratio of spin label to BBM lipid was about 1:100.

BBMV were then incubated with increasing concentrations of radiolabeled sodium cholate at room temperature for 15 min.

After incubation BBMV were pelleted by centrifugation at 80000 g for 10 min. thus isolating a complex BBMV associated with bile salt. The quantity of bile salt associated with BBMV was determined by measuring the amount of radiolabeled sodium cholate present in the BBM pellet.

In this way the amount of cholate associated with BBMV was determined as a function of the total sodium cholate concentration (FIG. 1). As shown in this figure, at sodium cholate concentrations >8 mg/ml (~19 mM) the amount of BBMV pelleted by centrifugation at 80000 g for 10 min. decreased due to solubilization of the BBM (cf. dashed line in FIG. 1). The sodium cholate concentration obtained by extrapolation of the dashed line to the x-axis is taken as the total bile salt concentration required to solubilize the BBM.

The solubilization of BBMV in the presence of excess bile salt was also monitored by light-scattering. For this purpose, BBMV at 2.34 mg protein/ml were suspended in Hepes/Tris buffer and incubated with bile salt of a given concentration at room temperature for 15 min. After incubation, the absorbance of the dispersion was measured at 400 nm.

ESR spectra were then recorded at 9.2 GHz with a Varian X-band spectrometer (Model E-104 A) equipped with a variable temperature control (for details see Thurnhofer, H. and Hauser, H. 1990. *Biochim. Biophys. Acta* 1024, 249–262). Order parameters S were directly derived from the ESR spectra (Hauser, H. Gains, N., Semenza, G., and Spiess, M. 1982. *Biochemistry* 21, 5621– 5628).

The lipid content of BBMV was determined gravimetrically after extraction of the lipids into hexane-2-propanol (3:2, v/v) according to Radin, A. (1981) *Methods Enzymol.* 72, 5–7. Lipid phosphorus was determined according to Chen, P. S., Toribara, T. Y., and Warner, H. 1956. *Anal. Chem.* 28, 1756–1758). The protein concentrations were determined by the bicinchoninic acid method using bovine serum albumin as a standard (Smith, P. K., Krohn, R. I., Hermanson, G. T., Malia, A. K., Gartner, F. H., Provenzano, M. D., Fujimoto, E. K., Goeke, N. M., Olson, B. J., and Klenk, D. C. 1985. *Anal. Biochem.* 150, 76–85).

Thin-layer chromatography was carried out as described by Hauser et al. 1980. *Biochim. Biophys. Acta* 602, 567–577.

Since experiments were carried out only with small intestines, an important question which remained was whether the bile salt transporter, (a membrane protein in the brush border membrane of ileum which is responsible for the active transport of bile salt from the intestinal lumen to the enterocyte and is an Na+ dependent bile salt transport protein) is responsible for the effect observed. Experiments were conducted to show that bile salt binding to brush border membrane is not restricted to ileum, but is observed with other intestinal segments and thus to show that the bile salt transporter is not responsible for the effect. Because of the importance of the question the problem was addressed in both in an in-vitro and in vivo system. Jejunal and ileal segments of both rabbit and pig were used. Prepared brush border vesicles were used as an in vitro system and isolated enterocytes were used as an in vivo testing system.

The results obtained from this experimentation may be summarized as follows:

(I) Isolated enterocytes closely resembled brush border membrane vesicles regarding the binding of sodium cholate. In all other properties tested so far, isolated enterocytes paralleled brush border membrane vesicles. These include the fast, protein-mediated uptake of cholesterol from bile salt micelles.

(II) Brush border membrane vesicles of ileal origin bound somewhat more bile salt/mg protein than vesicles prepared from jejunal segments.

(III) There was no significant difference in the binding of bile salts/mg protein between enterocytes prepared form ileum and jejunum.

In summary this series of experiments clearly shows that the property of bile salt binding cannot be attributed to a bile salt transporter membrane protein in the brush border membrane of ileum. On the contrary, the capacity of bile salt binding to BBM protein seems to be distributed over the entire small intestines. Thus bile salts specifically bind to intestinal brush border membrane protein.

DETAILED DESCRIPTION OF DRAWINGS

FIG. 1 shows an isotherm describing the interaction of sodium cholate with BBMV. BBMV at 1 mg protein/ml were incubated with increasing concentrations of $^{14}C$-labeled sodium cholate at room temperature for 20 min. After incubation BBMV were separated from bile salt micelles by centrifugation at 80000 g in a Beckman airfuge for 10 min. and the radioactivity present in BBM pellet and the supernatant was determined.

The radioactivity represents the amount of cholate associated with the BBM which is expressed as mg cholate/mg BBM protein and plotted as a function of the total cholate concentration. The dotted line is explained in the text.

Figure 2:
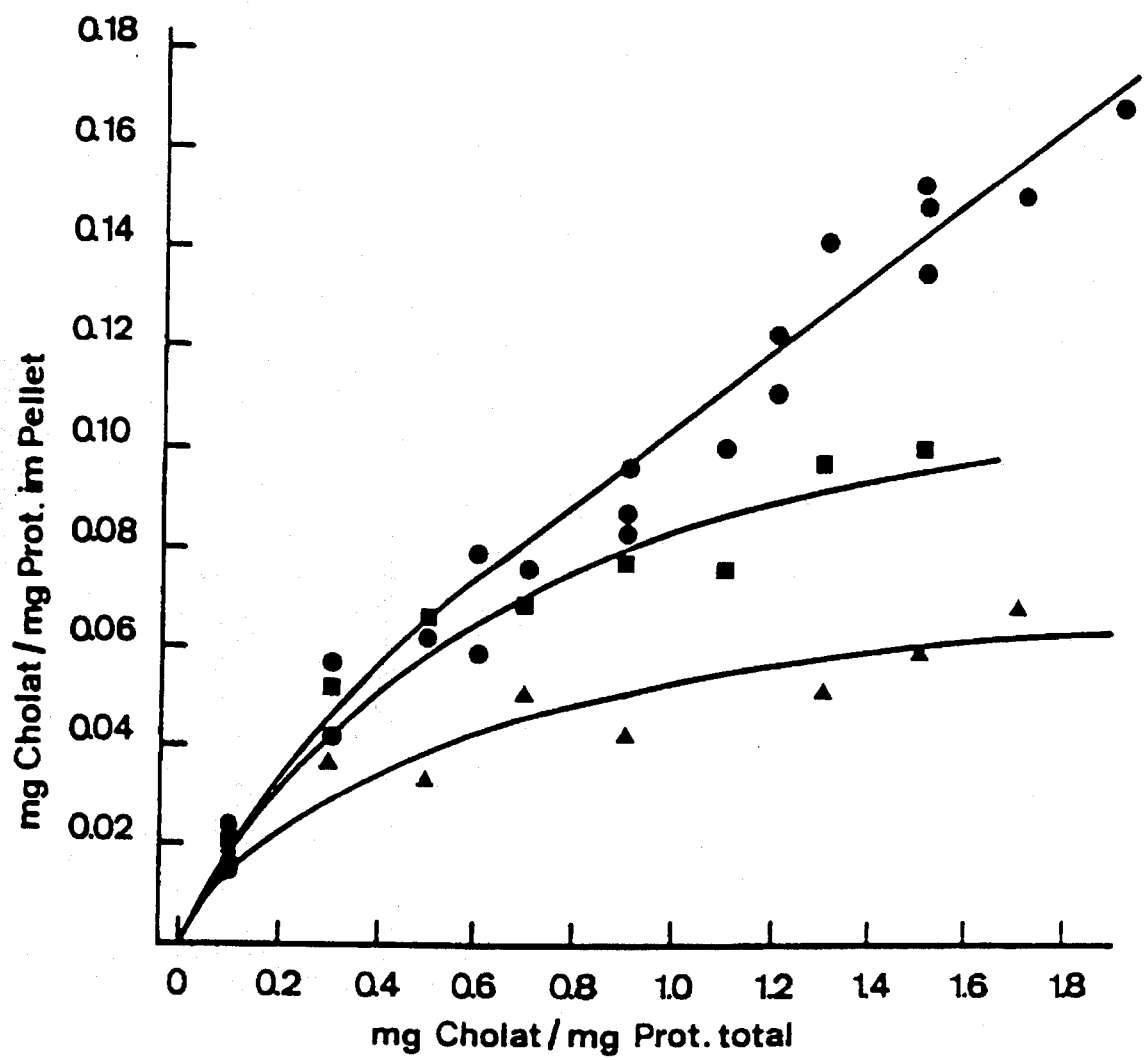
FIG. 2 shows isotherms for the interaction of sodium cholate with intact and pretreated BBMV.

FIG. 2 shows isotherms for the interaction of sodium cholate with intact and pretreated BBMV. BBMV at 12.3 mg protein/ml were incubated with increasing concentrations of $^{14}C$-labeled sodium cholate and the amount of bile salt associated with the BBM was determined as described in the legends to FIG. 1 (cf. materials and methods above). The isotherms shown in this figure were recorded with intact BBMV (●—●), with BBMV that were thawed and stored for 2 hours at room temperature before the measurement (■—■) and with BBM that were treated with proteinase K (▲—▲) prior to recording the isotherm.

Figure 3:
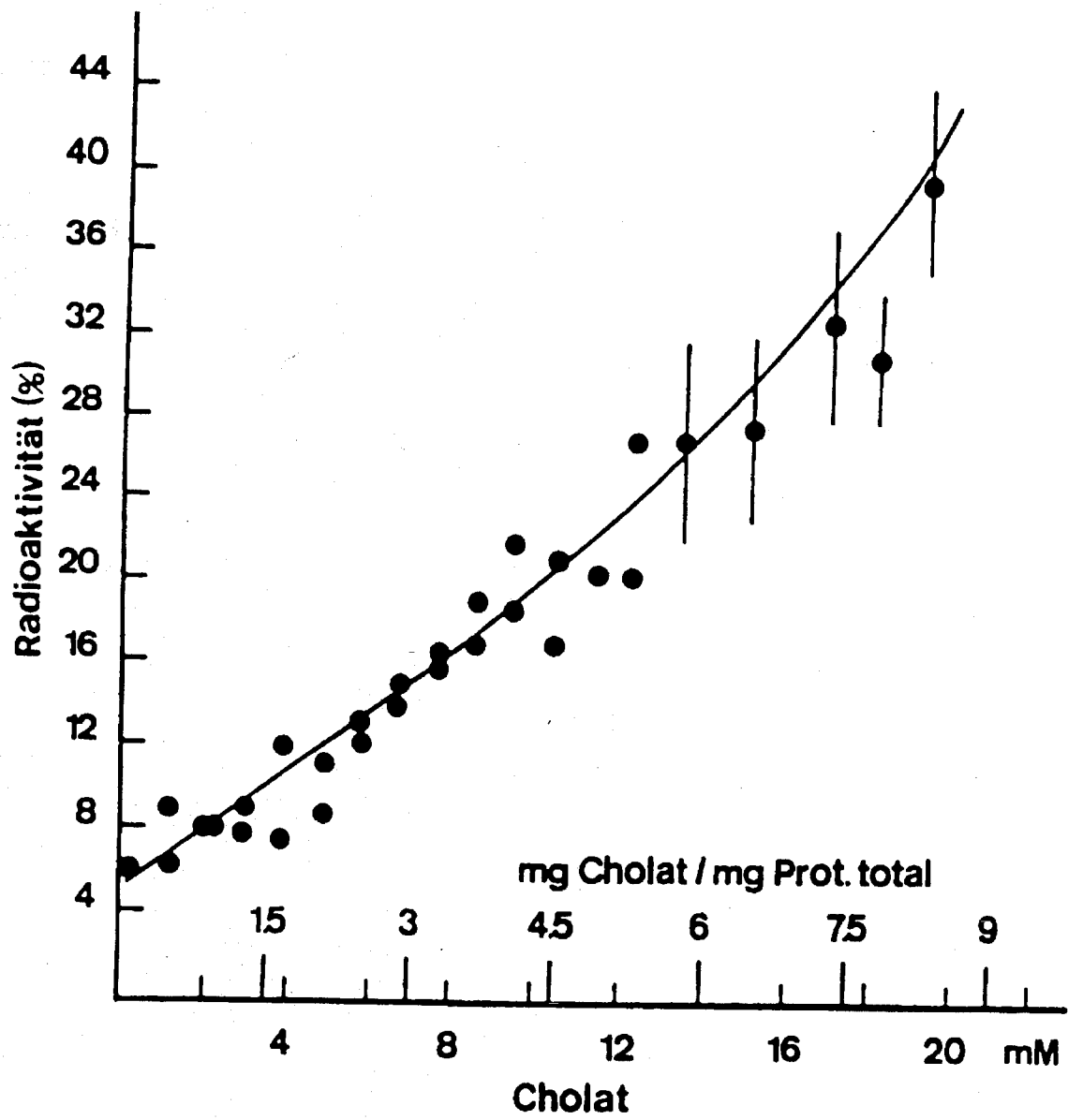
FIG. 3 shows loss of radiolabeled PC from BBMV as the result of the interaction of BBMV with bile salt micelles.

FIG. 3 shows loss of radiolabeled PC from BBMV as the result of the interaction of BBMV with bile salt micelles. BBMV were labeled with $^{3}H$-DPPC as described in Materials and Methods. The radiolabeled BBMV at 1 mg protein/ml were incubated with increasing concentrations of sodium cholate at room temperature for 20 min.

After incubation BBMV were separated from bile salt by centrifugation at 80000 g for 10 min., and the radioactivity present in the supernatant was determined and expressed as %. Large variations in the data were observed at total cholate concentration >12 mM, and in this concentration range the data are presented as the mean with the bar representing the experimental scatter.

Figure 4:
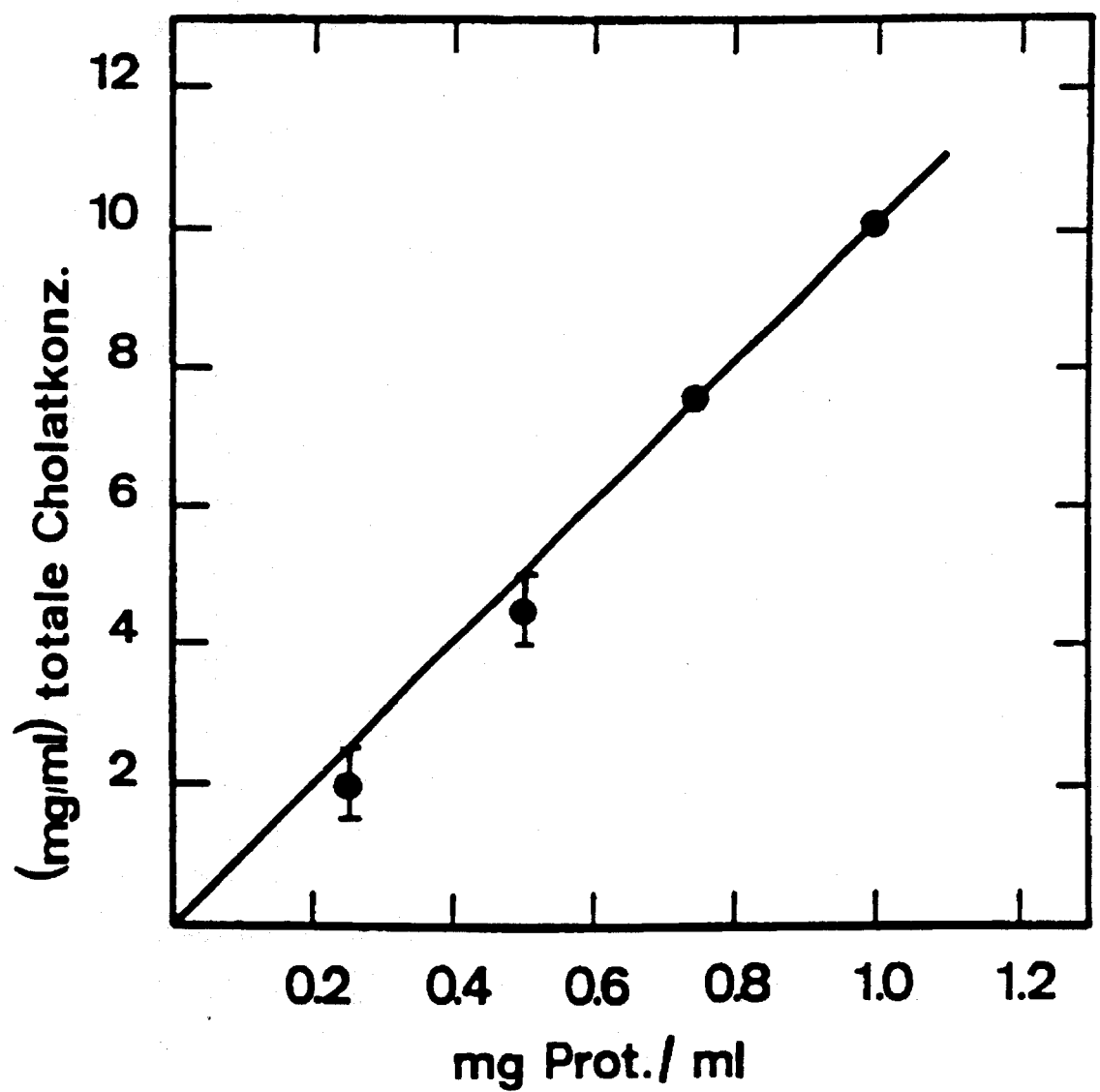
FIG. 4 shows solubilization of BBMV by sodium cholate.

FIG. 4 shows solubilization of BBMV by sodium cholate. The total sodium cholate concentration required to solubilize BBMV was determined as a function of the BBM concentration expressed in mg protein/ml. The total sodium cholate concentration at which solubilization occurred was determined as described in FIG. 1 and in the Materials and Methods section above.

Figure 5:
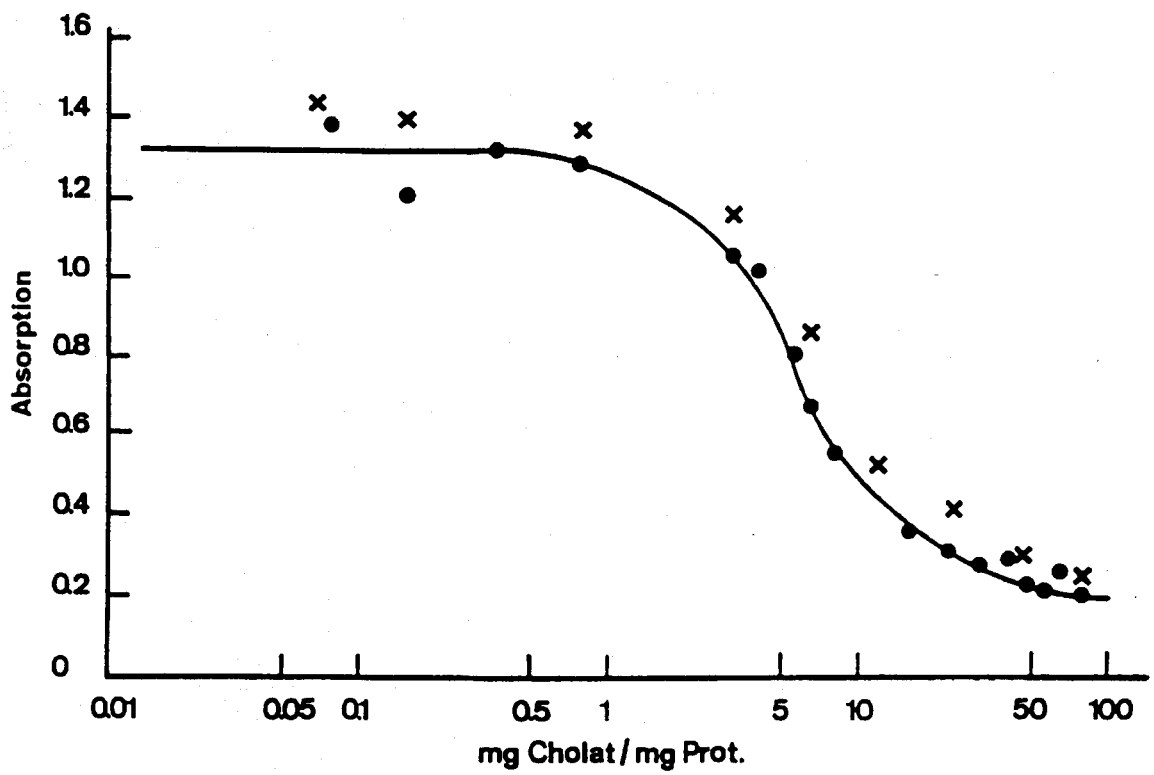
FIG. 5 shows solubilization of BBMV in the presence of bile salt micelles as monitored by light-scattering.

FIG. 5 shows solubilization of BBMV in the presence of bile salt micelles as monitored by light-scattering. The absorption of light at 400 nm of BBMV suspensions at 1.23 mg protein/ml was determined at room temperature as a function of the total sodium cholate (●—●) and sodium taurocholate concentration (x—x). BBMV suspended in Hepes (N-(2-hydroxyethyl)piperazine-N'-2-ethane sulfonic acid) buffer were incubated with the appropriate bile salt concentration at room temperature for 15 min. and the absorbance at 400 nm was measured in a Zeiss spectrophotometer.

FIG. 6 shows ESR spectra of BBMV labeled with 5-doxyl-PC. ESR spectra of BBMV (12.3 mg protein/ml) were recorded at room temperature (A) and after incubation of the BBMV with sodium cholate micelles at room temperature for 20 min. ESR spectra were recorded of BBMV incubated with sodium cholate micelles at 6.2 mg/ml (=14.3 mM) in B, at 18.5 mg/ml (=43 mM) in C, 31 mg/ml (=71.5 mM in D and 129 mg/ml (=0.3M) in E.

Figure 7:
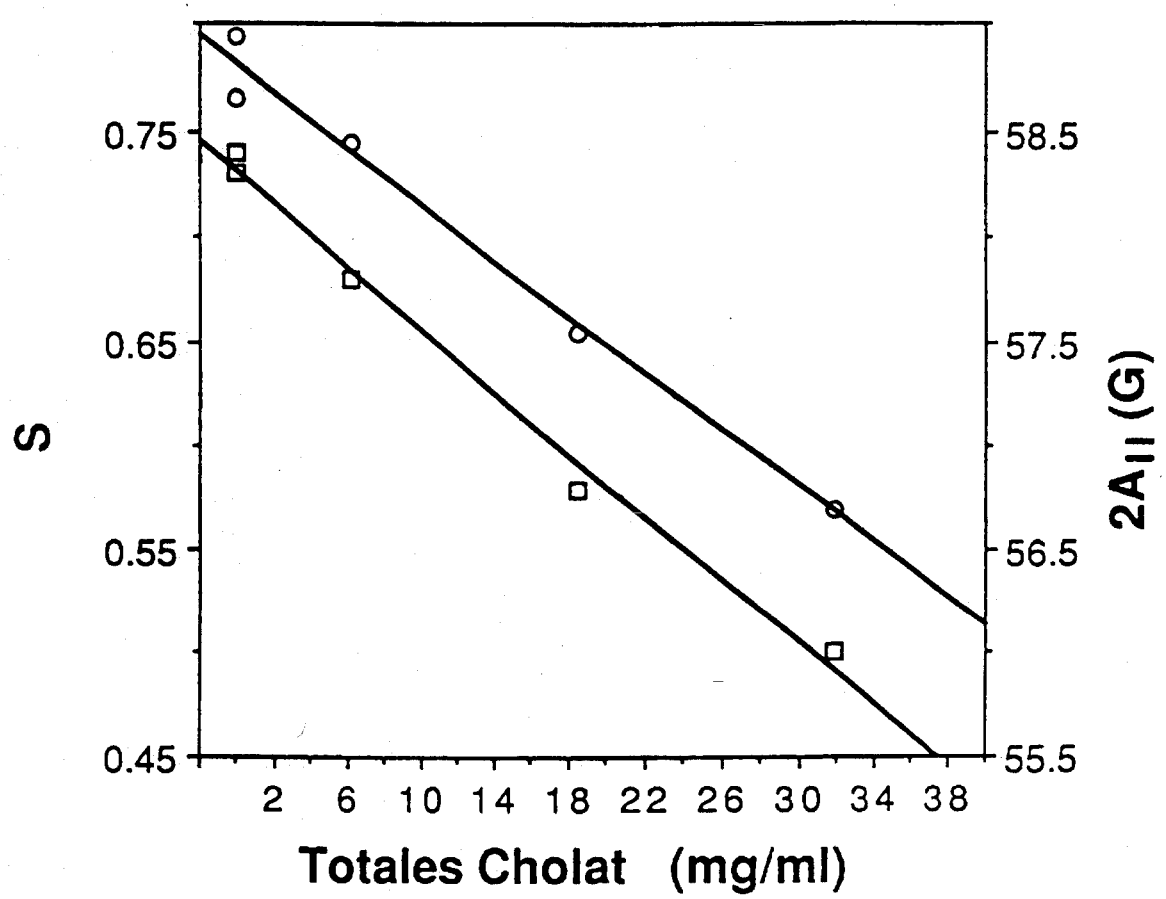
FIG. 7 shows maximum hyperfine splittings $2 A_{11}(G)$ (□) and order parameters S (o) of spin-labeled BBMV as a function of the total sodium cholate concentration in mg/ml.

FIG. 7 shows maximum hyperfine splittings $2 A_{11}(G)$ (□) and order parameters S (o) of spin-labeled BBMV as a function of the total sodium cholate concentration in mg/ml.

The hyperfine splitting values $2 A_{11}$ and $2 A\perp$ were directly taken from the ESR spectra shown in FIG. 6 and order parameters were calculated using these values as described by Hauser, H. Gains, N., Semenza, G., and Spiess, M. 1982. *Biochemistry* 21, 5621–5628. The solid lines were fitted to the experimental data by linear regression analysis. The straight lines thus obtained were $y=58.3-0.0751\times(r^2=0.992)$ for the maximum hyperfine splitting $2 A_{11}$ and $y=0.78-(6.69\times10^{-3})\times(r^2=0.987)$ for the order parameter.

Isotherms Describing the Interaction of Bile Salts with Rabbit Intestinal BBM BBMV at 1 mg protein/ml were incubated with radiolabeled bile salt micelles (20 mM) as described in Materials and Methods set forth above and the amount of bile salt associated with the BBMV was determined as a function of time. A typical saturation curve was obtained indicating that equilibrium was reached after about 10 min.

In FIGS. 1 and 2 the amount of sodium cholate associated with BBM was determined after incubation of BBMV with bile salt at room temperature for 20 min. FIG. 1 shows that the amount of sodium cholate associated with the BBM increased linearly with the total bile salt concentration up to about 8 mg cholate/ml (~19 mM).

The linear relationship up to this concentration (see solid line in FIG. 1) indicates that on the average 7±0.5% of the total cholate added is associated with the BBMV. At sodium cholate concentrations exceeding this concentration a steep decrease in the amount of bound cholate was observed (cf. dashed line, FIG. 1). At cholate concentrations greater than 11 mg/ml (=25.5 mM) no BBM pellet formed upon centrifugation at 80000 g for 10 min. indicating that BBMV were solubilized to smaller particles including mixed bile salt micelles.

More isotherms characterizing the interaction of bile salt with the rabbit intestinal BBM are shown in FIG. 2. In these examples either intact or pretreated BBMV, all at 12.3 mg protein/ml, were used. Intact BBMV were freshly thawed and immediately processed (circles), pretreated BBMV comprise vesicles that were thawed and stored at room temperature (squares) and BBMV treated with proteinase K (triangles) prior to the interaction with bile salt.

From an inspection of FIG. 2 it is clear that BBMV treated with proteinase K bind significantly less cholate than intact BBMV. The isotherm of BBM incubated at room temperature lies between that of intact and the proteolytically treated BBMV.

More importantly, BBMV stored at room temperature or treated with proteinase K show saturation; the amount of bound cholate levels off at total cholate concentrations 1 mg cholate/mg BBM protein. This is contrasted by intact BBMV that exhibited a linear relationship between bound and total cholate concentrations above a total cholate concentration of about 0.5 mg cholate/mg protein (FIG. 2). BBMV were in excess so that no solubilization of the BBM occurred over the concentration range of cholate used. For the linear portion of the isotherm of intact BBMV (circles the bound cholate amounted to 10±1% of the total cholate added.

BBMV were radioactively labeled with $^{3}H$-DPPC (1,2-dipalmitoyl-sn-phosphatidylcholine) and the interaction of these BBMV with increasing concentrations of sodium cholate was investigated.

FIG. 3 shows that with increasing bile salt concentrations more and more radiolabeled $^{3}H$-DPPC was distributed into the bile salt micelles. It is clear that the curve in FIG. 3 does not go through the origin. About 5% of the radioactivity is apparently released from the BBM into the aqueous phase even in the absence of bile salt. This result may be due to a water-soluble degradation product of the label.

The amount of radiolabeled lipid distribution into the bile salt micelles increased approximately linearly with total bile salt concentration: at 20 mM total sodium cholate about 45% of the radioactivity was present in the bile salt micelles (FIG. 3).

Suspensions of BBMV differing in BBM concentration were treated with increasing concentrations of $^{14}$C-labeled sodium cholate as shown in FIG. 1. The isotherms were recorded and the bile salt concentration was determined at which no BBM pellet formed upon centrifugation at 80000 g for 10 min. and solubilization of BBM occurred. The concentration at which solubilization occurred was determined as shown in FIG. 1: this concentration is identical to that obtained by extrapolating the dotted line in FIG. 1.

The values thus obtained are plotted in FIG. 4 as a function of the BBM concentration expressed as mg protein/ml. A linear relationship resulted with a slope of 10±1 mg sodium cholate/mg BBM protein. Hence, BBMV are solubilized with a tenfold amount of cholate referred to the protein concentration of BBM or with a twentyfold excess of sodium cholate referred to the total lipid concentration of BBM.

Solubilization of BBMV or excess bile salt was readily followed by light-scattering. In FIG. 5, the absorption of light at 400 nm of BBM dispersions at 1.23 mg protein/ml is plotted as a function of the total bile salt concentration. The absorption due to light-scattering remained unchanged up to bile salt concentrations of ~1 mg/mg protein. At higher bile salt concentrations there is a decrease in absorbance for both cholate and taurocholate (FIG. 5).

The inflexion points of the sigmoidal curves shown in FIG. 5 are at 6.9 mg/ml (16 mM) and 7.9 mg/ml (17.5 mM) for sodium cholate and sodium taurocholate, respectively. At bile salt concentrations of 50 mg/mg BBM protein the value of absorbance is about 0.2 characteristic of small micelles. Electron microscopy of freeze-fractured samples show that under these experimental conditions indeed small micelles are present with a diameter less than ~13 nm.

The light-scattering data of FIG. 5 are in agreement with the results of the solubilization of BBMV summarized in FIG. 4. For instance, incubation of BBMV with a tenfold excess of sodium cholate (relative to the protein content of BBM) at room temperature for 15 min. reduced the absorbance to 30% of its original value indicating that most of the BBMV are solubilized to small mixed micelles.

For the data of FIGS. 4 and 5, the present inventors conclude that BBMV at concentrations of ~1 mg protein/ml as routinely handled are solubilized by bile salt concentrations of ≧10 mg/ml (~23 mM). This is a multiple of the critical micellar concentration (CMC) of bile salts which is in the range of 2 to 6 mM (Hoffmann, A. F., and Small, D. M. 1967. *Ann. Rev. Med.* 18, 333–376).

Figure 6A:
FIG. 6 shows ESR spectra of BBMV labeled with 5-doxyl-PC.
Figure 6B:
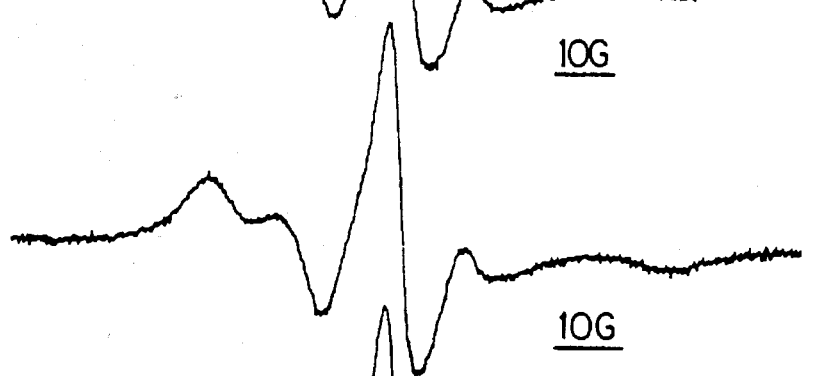

ESR spectra of BBMV spin-labeled with 5-doxyl-PC were recorded before and after incubation with sodium cholate. The line shape of the ESR spectrum of BBMV labeled with 5-doxyl-PC is characteristic of rapid but highly anisotropic motion of the spin probe (FIG. 6A). The maximum hyperfine splitting 2 A is a measure of the anisotropy of motion and the value obtained is 2 $A_{11}$=58.4G. The order parameter S derived from the spectrum in FIG. 6A is S=0.78±0.02 which is in good agreement with published results (Hauser, H. Gains, N., Semenza, G., and Spiess, M. 1982. *Biochemistry* 21, 5621–5628).

Incubation of spin-labeled BBMV with sodium cholate produced spectral changes: with increasing total sodium cholate concentration the spectral anisotropy decreased.

The line shape of the ESR spectra observed in excess sodium cholate (0.13 g/ml=0.3M) (FIG. 6E) is very similar to that obtained when 5-doxyl-PC was present in micelles of pure cholate, deoxycholate, glycocholate and taurocholate (all as the sodium salt). The line shape is consistent with spherical or disk-shaped micelles (Lasic, D. D. and Hauser, H. 1985. *J. Phys. Chem.* 89, 2648–2651). The residual anisotropy measured in the ESR spectrum of FIG. 6E is 2 $A_{11}$=35.5 G agrees with values measured for 5-doxyl-PC in pure bile salt micelles which ranged between 35.5 and 36.8 G.

Figure 6C:
Figure 6D:

Spin-labeled BBMV at 12.3 mg protein/ml incubated with sodium cholate micelles at bile salt concentrations ≧10 mg/ml gave composite ESR spectra consisting of a highly anisotropic component and a second almost isotropic one (cf. FIGS. 6C and 6D).

Figure 6E:
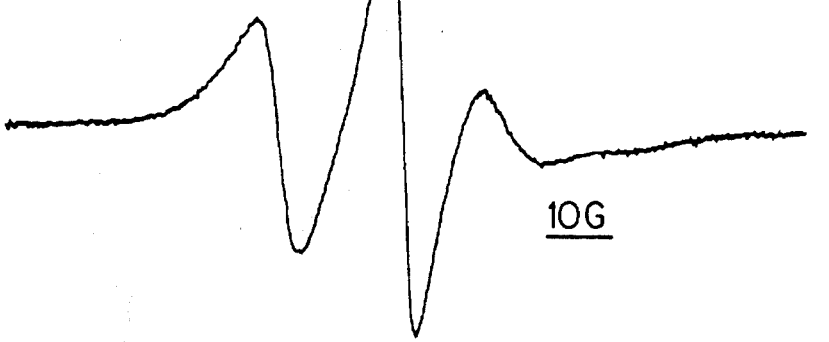

By comparison with the ESR spectra of FIG. 6A and 6E the anisotropic component can be assigned to the presence of spin label in the lipid bilayer of the BBM and the second component to spin label being present in mixed bile salt micelles. At sodium cholate concentrations greater than 55 mg/ml (≈130 mM) the isotropic component is dominant (FIGS. 6D and 6E).

The ESR spectra shown in FIG. 6 were evaluated in terms of maximum hyperfine splittings 2 $A_{11}$ and order parameters S. Both these parameters decreased linearly with increasing total cholate concentration (FIG. 7).

The binding isotherms shown in FIGS. 1 and 2 give the total amount of the bile salt associated per mg of BBM protein. This amount comprises bile salt incorporated into the lipid bilayer of BBM as well as bile salt which may be adsorbed or bound to the membrane protein surface.

Evidence that bile salts are indeed incorporated in the lipid bilayer of BBMV and associated with BBM protein was provided by ESR spin labeling. Previous ESR studies showed that the spin label 5-doxyl-PC is indeed incorporated into the lipid bilayer of BBMV and hence probing the fluidity of the lipid bilayer of BBM (Hauser, H., Gains, N., Semenza, G. and Spiess 1982.M. *Biochemistry* 21, 5621–5628;Mütsch, B., Gains, N., and Hauser, H. 1983. *Biochemistry* 22, 6326–6333).

The ESR spectra of BBMV spin-labeled with 5-doxyl-PC indicate that the incorporation of cholate into the lipid bilayer perturbs the lipid packing and as a result the anisotrophy of the molecular motion of the membrane lipids decreases (FIG. 6). This is documented by the linear decrease of both the maximum hyperfine splitting 2 $A_{11}$ and the order parameter S (FIG. 7).

Thus the present invention includes a method for detecting specific binding of bile salts to intestinal brush border membrane protein, which includes a) suspending an intestinal brush border membrane (BBM) sample in a suitable buffer, b) incubating said BBM with suitable concentrations of radiolabeled bile salt at room temperature for a suitable period of time, c) centrifuging said BBM incubated with radiolabelled bile salt at about 80000 g for about 10 min. d) measuring the amount of radiolabelled bile salt present in the BBM to determine the amount of bile salt associated with the BBM.

It is concluded that some bile salt is incorporated into the lipid bilayers of the BBM. This is consistent with $^1$H NMR evidence (Tellier, C., Vallet-Strouve, C., Akoka, S., and Poignant, S. 1987. *Eur. Biophys. J.* 15, 177–184). Consistent with the ESR results is also the finding that the active transport of glucose across the BBM in the presence of a $Na^+$ gradient as the driving force of the glucose transport breaks down.

It is found that the total amount of bile salt associated with BBMV and its proteins depends sensitively on the state of the BBM as demonstrated in FIG. 2. Proteolytic treatment of BBMV with proteinase K leads to a significant reduction in the amount of bile salt bound to BBM protein (FIG. 2). Storing of BBMV at room temperature was shown to liberate proteins from the BBM (Thurnhofer, H. and Hauser, H. 1990. *Biochim. Biophys. Acta* 1024, 249–262) and after such a treatment BBMV bind significantly less bile salt than intact BBMV.

The more protein is lost from the BBM by proteolysis, the less bile salt is bound to the membrane. This result has been obtained reproducibly. It has been observed with many different preparations of BBMV and probably accounts for the large experimental scatter and variability encountered when binding isotherms are recorded with different BBM preparations.

The results shown in FIG. 2 are of physiological importance and are not noted in the prior art. The data presented in FIG. 2 indicate that a significant portion of the bile salt associated with BBM is adsorbed or bound to protein(s) and/or glycoprotein(s) exposed on the membrane surface. The isotherm obtained for BBMV treated with proteinase K represents the distribution of bile salt into the lipid bilayer of the BBM. This isotherm (cf. triangles of FIG. 2) differs in shape from that of intact BBM (cf. circles of FIG. 2): the former shows saturation at total cholate concentrations >1.8 mg cholate/mg BBM protein and the amount of cholate associated with the proteolytically treated BBMV at 1.8 mg total sodium cholate/mg BBM protein is 2–3 times less than that associated with intact BBMV.

This means that more than half of the bile salt present in BBM is associated with BBM protein and not incorporated in the lipid bilayer of the BBM. These results are at variance with a previous study by Wilson and Treanor who concluded that the interaction of $^{14}$C-labeled taurodeoxycholate with BBM from rat small intestines is unspecific and independent of membrane proteins. Wilson et al. merely reflected the interaction of the bile salt with the lipid bilayer of the BBM. Their conclusions are mainly based on the finding that boiling of the suspension of BBMV and proteolysis of BBM with trypsin had no effect on the extent of binding of the bile salt.

Considering the isotherms in FIGS. 1 and 2 together with the result of FIG. 3, it is clear that, in the presence of bile salt micelles, bile salts are not only incorporated into the lipid bilayer of the BBM but phospholipids are also distributed from BBMV into the micellar phase.

The radiolabeled DPPC may be regarded as a lipid marker of the bilayer of the BBM. The marked loss of $^3$H-DPPC from BBMV in the presence of an excess bile salt micelles indicates that probably other lipids of the BBM are also distributed into the micellar phase. This expectation is borne out by experiment.

After incubation of BBMV with bile salt micelles, BBMV were separated from the bile salt micelles by centrifugation at 80000 rpm for 10 min. and the lipids of the micellar phase were extracted according to Bligh et al. (Bligh, E. G., and Dyer, W. J. 1959. *Can. J. Biochem. Physiol.* 37, 911–917).

Thin-layer chromatography analysis of the lipid extract confirmed that all lipids including glycolipids of the BBM were present in the micellar phase. The results indicate that at equilibrium BBM, lipids are distributed between the membrane and the micellar phase. This conclusion is consistent with $^{31}$P NMR measurements (Tellier, C., Vallet-Strouve, C., Akoka, S., and Poignant, S. 1987. *Eur. Biophys. J.* 15,177–184; Vallet-Strouve, C., Tellier, C., Poignant, S., and Boucrot, P. 1985. *J. Membrane Biol.* 84, 73–79). These authors showed that the integrity of BBMV (12.5 mg total lipid/ml) prepared from rabbit small intestines is maintained in the presence of 10 mg sodium cholate/ml (=18 mM).

After incubation of the BBMV with the bile salt micelles 18% of the phospholipids were transferred to the micellar phase giving rise to an isotropic sharp $^{31}$P NMR signal.

The data of FIGS. 1–3 and the results discussed above are pertinent to the mechanism of the solubilization of BBMV in excess bile salt. Regarding this mechanism, BBMV behave differently from phospholipid vesicles as well as red blood cell membranes. The phase diagram of the three-component system sodium cholate-egg phosphatidylcholine-$H_2O$ is available (cf. Small, D. M., Bourges, M., and Dervichian, D. G. 1966. *Nature* 211,816–818; Hoffmann, A. F., and Small, D. M. 1967. *Ann. Rev. Med.* 18, 333–376).

In this phase diagram the boundary between the lamellar and the micellar phase is practically identical with the line characteristic of a bile salt/egg PC mole ratio of 2. At this composition, the phase transition lamellar-to-micellar phase sets in, and at higher bile salt concentrations mixed micelles are present (Shankland, W. 1970. *Chem. Phys. Lipids* 4, 109–130). for instance, multilamellar egg PC vesicles of 10 mg lipid/ml (=13.3 mM) are solubilized by a total sodium cholate concentration of 30 mM (Brunner, J., Hauser, H., and Semenza, G. 1978. *J. Biol. Chem.* 253, 7538–7546).

This concentration consists of the CMC and the amount of cholate present in the egg PC bilayers. Egg PC bilayers at concentrations <1 mg lipid/ml are solubilized at total sodium cholate concentrations close to the CMC of the bile salt (Lichtenberg, D. 1985. *Biochim. Biophys. Acta* 821, 470–478; Almog, S., Litman, B. J., Wimley, W., Cohen, J., Wachtel, E. J., Barenholz, Y., Ben-Shaul, A., and Lichtenberg, D. 1980. *Biochemistry,* 29, 4582–4592; Saito, H., Sugimoto, Y., Tabeta, R., Suzuki, S., Izumi, G., Kodama, M., Toyoshima, S. and Nagata, G. 1983. *J. Biochem.* 94, 1877–1887 showed that deoxycholate and chenodeoxycholate as the sodium salts induced complete hemolysis in fresh human erythrocytes at about 1 mM concentrations of bile salt while sodium cholate exhibited a comparable effect at 5 mM concentrations. While the solubilization of phospholipid bilayers and the hemolysis of red blood cell membranes occur at total bile salt concentrations close to the CMC or even below, the solubilization of BBM requires an excess of bile salt micelles.

BBMV at 1 mg protein/ml are solubilized at a total sodium cholate concentration of 10 mg cholate/mg protein, corresponding to a concentration of 23 mM which is almost four times the CMC (critical micellar concentration). This stresses the resistance of the BBM towards bile salts, a result which is not surprising considering that the bile salt concentration in the upper small intestines ranges from 4–12 mM reaching extreme values of 20–25 mM.

The results also suggest that the mechanism of solubilization of BBM is different from the solubilization of phospholipid bilayers and possibly other biological membranes. With model membranes the prevailing view is that bile salts are distributed between the lipid bilayers and the surrounding aqueous phase until the lipid bilayers are saturated with the bile salt. This occurs usually at a monomeric bile salt concentration which is close to or even below the CMC. At these bile salt concentrations the phospholipid bilayers disintegrate to small mixed micelles.

In contrast, BBMV are stable at the CMC of bile salts. As shown in FIG. 3 and discussed above, lipids and probably also proteins of the BBM are distributed between the membrane and the micellar phase. With increasing bile salt concentrations, the volume fraction occupied by the bile salt micelles grows and in excess bile salt the distribution of membrane components is in favor of the micellar phase.

Both the incorporation of bile salt into the BBM as well as the concomitant extraction of membrane components into the micellar phase affect the membrane stability. In excess bile salt these two processes progress to the extent that the integrity of the BBM is no longer warranted and eventually the membrane structure disintegrates to mixed bile salt micelles.

The difference in the solubilization mechanism between simple phospholipid bilayers and probably also other biological membranes on the one hand and BBM on the other is due to the resistance of BBM towards bile salt. Phospholipid bilayers and red blood cell membranes appear to be saturated with bile salts at much lower free bile salt concentrations than BBM. The latter membrane apparently resists bile salt concentrations which are a multiple of the CMC, i.e., under these conditions less bile salt is incorporated into BBM compared to phospholipid bilayers and red blood cell membranes. The structural principle underlying this marked resistance is unknown presently. BBM has been shown to contain tightly packed lipid bilayers (Brasitus, T. A., Tall, A. R., and Schacter, D. 1980. *Biochemistry* 19, 1256–1261; Hauser, H. Gains, N., Semenza, G., and Spiess, M. 1982. *Biochemistry* 21, 5621–5628). The tight packing of the BBM together with the molecular shape and polarity of the bile salt molecule might be responsible for the sluggish incorporation of this molecule into BBM. It is conceivable that the peculiar molecular shape resulting from the cis fusion of the A/B rings and the polarity of the alicyclic ring system of bile salts are unfavorable parameters rendering the incorporation of these molecules into tightly packed lipid bilayers more difficult.

Thus the interaction of bile salts with BBM is partly protein-mediated and not only due to a nonspecific distribution of bile salt between the lipid bilayer of the BBM and the aqueous phase. This result is at variance with previous work by Wilson and Treanor (Wilson, F. A., and Treanor, L. L. 1979. *J. Membrane Biol.* 33, 213–230), who were unable to detect any specific binding of bile salts to rat intestinal BBM.

The discovery that the interaction of bile salts with BBM is partly protein-mediated allows for a method for diagnosing irregularities in bile salt absorption via proteins on intestinal brush border membrane. Thus, the method according to the present invention includes steps of a) suspending an intestinal brush border membrane (BBM) sample to be tested in a suitable buffer; b) incubating said BBM with suitable concentrations of radiolabeled bile salt at room temperature for suitable period of time; c) centrifuging said BBM incubated with radiolabelled bile salt at about 80000 g for about 10 min. d) measuring the amount of radiolabelled bile salt present in the BBM to determine the amount of bile salt associated with the BBM protein; and e) comparing the amount measured in step (d) with a standard bile salt-BBM protein association value wherein a deficiency in said values represents an irregularities in bile salt absorption via proteins on intestinal brush border membrane.

In a preferred embodiment of the above method the bile salt is cholate, deoxycholate, chenodeoxycholate, taurocholic and glycocholic acids or sodium salts or mixtures thereof. More preferred is a bile salt of sodium cholate.

EXAMPLE

A sample of brush border membrane to be tested is suspended in 0.01M Hepes buffer adjusted with Tris to pH 7.5 and containing 0.3M mannitol, 5 Mm EDTA and 0.02% $NAN_3$.

The sample is then incubated with a concentration of radiolabeled sodium cholate at room temperature for 15 min.

After incubation, the sample is pelleted by centrifugation at 80000 g for 10 min., isolating the BBM protein associated with bile salt. The quantity of bile salt associated with the BBM sample is determined by measuring the amount of radiolabeled sodium cholate associated with the BBM protein pellet.

This value is compared with a standard bile salt-BBM protein association value. A deficiency in the values represents irregularity in bile salt absorption via proteins on intestinal brush border membrane.

As will be apparent to those skilled in the art in the light of the foregoing disclosure, many alterations, modifications and substitutions are possible in the practice of this invention, without departing from the spirit or scope thereof. All publications discussed herein are hereby incorporated by reference.

I claim:

1. A method for detecting irregularities in bile salt absorption via proteins of the intestinal brush border membrane comprising the steps of:

a) suspending an intestinal brush border membrane vessicle (BBMV) sample in a suitable buffer, b) incubating said BBMV sample with suitable concentrations of radiolabelled bile salt at room temperature for suitable period of time, c) centrifuging said BBMV sample incubated with radiolabelled bile salt at about 80000 g for about 10 min. to separate BBMV from bile salt associated with brush border membrane (BBM) protein, d) measuring an amount of radiolabelled bile salt associated with the BBM protein, and e) comparing the amount measured in step (d) with a standard bile salt-BBM protein association value wherein a discrepancy in said measured amount of step (d) and said standard bile salt-BBM protein association value represents an irregularity in bile salt absorption via proteins on intestinal brush border membrane.

2. The method according to claim 1, wherein said bile salt is selected from the group consisting of cholate, deoxycholate, chenodeoxycholate, taurocholic and glycocholic acids and sodium salts and mixtures thereof.

3. A method for detecting specific binding of bile salts to intestinal brush border membrane protein, comprising the steps of a) suspending an intestinal brush border membrane vessicle (BBMV) sample in a suitable buffer;

b) incubating said BBMV sample with suitable concentrations of radiolabeled bile salt at room temperature for suitable period of time;

c) centrifuging said BBMV sample incubated with radiolabelled bile salt at about 80000 g for about 10 min. to separate BBMV from bile salt associated with brush border membrane (BBM) protein;

d) measuring an amount of radiolabelled bile salt associated with said BBM protein.

* * * * *